United States Patent
Govil et al.

(10) Patent No.: US 8,080,060 B2
(45) Date of Patent: Dec. 20, 2011

(54) PROCESSES AND SYSTEMS FOR LOADING MEDICAL IMPLANTS WITH SIMULATIVE GROWTH AGENTS

(75) Inventors: Amit Govil, San Diego, CA (US); Neil Irvin Thompson, San Marcos, CA (US); Christian Gabriel Gamboa, San Diego, CA (US); Sudhanshu Somasundar, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 169 days.

(21) Appl. No.: 12/251,297

(22) Filed: Oct. 14, 2008

(65) Prior Publication Data
US 2009/0098184 A1    Apr. 16, 2009

Related U.S. Application Data

(63) Continuation-in-part of application No. 12/130,920, filed on May 30, 2008.

(60) Provisional application No. 60/932,479, filed on May 30, 2007.

(51) Int. Cl.
*A61F 2/28* (2006.01)
*A61K 38/18* (2006.01)
*A61K 38/00* (2006.01)

(52) U.S. Cl. .................. 623/16.11; 623/23.61; 514/8.8; 514/8.9; 514/16.7

(58) Field of Classification Search ........................ None
See application file for complete search history.

(56) References Cited

U.S. PATENT DOCUMENTS

| | | | |
|---|---|---|---|
| 5,769,897 | A | 6/1998 | Harle |
| 5,997,895 | A | 12/1999 | Narotam |
| 6,648,133 | B1 | 11/2003 | Blaschke et al. |
| 7,045,125 | B2 | 5/2006 | Erbe et al. |
| 7,172,071 | B2 | 2/2007 | Hawkins |
| 7,198,150 | B1 | 4/2007 | Blaschke et al. |
| 2004/0230310 | A1 | 11/2004 | Ferree |
| 2005/0167309 | A1 | 8/2005 | Iwatschenko |
| 2006/0108239 | A1 | 5/2006 | Iwatschenko |
| 2006/0247783 | A1 | 11/2006 | McKay |
| 2007/0016215 | A1* | 1/2007 | Wilander et al. ............ 606/93 |
| 2007/0142916 | A1* | 6/2007 | Olson et al. ............ 623/17.11 |
| 2008/0025987 | A1 | 1/2008 | Beals et al. |

FOREIGN PATENT DOCUMENTS

| | | |
|---|---|---|
| WO | WO02/16209 | 2/2002 |
| WO | WO2005/037136 | 4/2005 |

* cited by examiner

*Primary Examiner* — Elizabeth C Kemmerer
*Assistant Examiner* — Xiaozhen Xie
(74) *Attorney, Agent, or Firm* — Michael R. Shevlin

(57) ABSTRACT

Methods and systems for providing an improved apparatus and packaging system to more expeditiously hydrate or reconstitute medical grafts and to effectively and uniformly seed the medical grafts with biological components and cells. The systems generally comprise a container comprising entry port, at least one substrate cavity, and top, side and bottom walls defining an inner surface. The entry port is configured to receive the biological solution. The cavity is in communication with the entry port and includes the porous substrate maintained under negative pressure. The container volume is substantially the same as a volume of the porous substrate. The side and bottom walls are configured to promote a laminar flow of the biological solution received through the entry port.

21 Claims, 8 Drawing Sheets

Figure 1A:
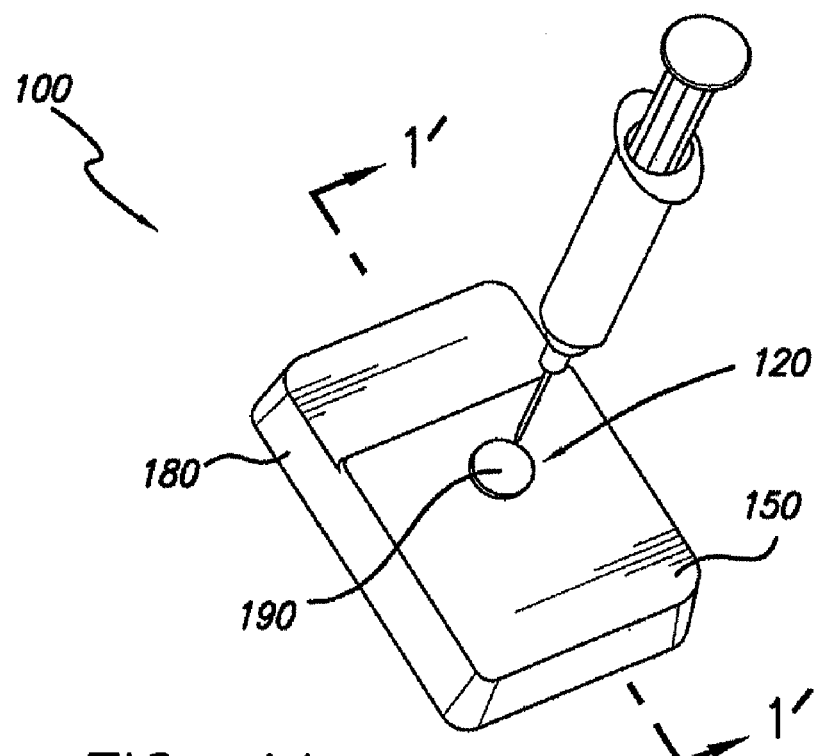

PROCESSES AND SYSTEMS FOR LOADING MEDICAL IMPLANTS WITH SIMULATIVE GROWTH AGENTS

CROSS-REFERENCE TO RELATED APPLICATIONS

This application is a continuation in part of U.S. application Ser. No. 12/130,920, filed on May 30, 2008 which claims priority pursuant to 35 U.S.C. § 119(e) to U.S. provisional application Ser. No. 60/932,479, filed May 30, 2007, which are hereby incorporated by reference in their entirety.

FIELD OF THE INVENTION

The present invention relates generally to medical implants and more particularly to methods and systems for hydrating and seeding medical implants with biological components.

BACKGROUND

Bone grafting refers to a wide variety of medical and dental surgical procedures by which the formation of new bone in a patient is augmented or stimulated. Bone grafting is used in many types of orthopedic procedures to treat bone fractures or loss, to repair injured bone that has not healed, and to fuse together joints to prevent movement. With particular reference to the spine, grafts have been used to stabilize the spine and to prevent movement by selected vertebral segments, which may be a significant cause of pain in some patients. Grafts have also been used to correct or stop the progress of spinal deformity, such as scoliosis, and to provide structural support for fractures of the spine.

Suitable grafts can be harvested from bones in the patient's own body (autografts), from bones in members of the same species (allograft), and from bones in members of other animal species (xenograft). Alternatively, bone grafts can be created from a wide variety of natural and/or synthetic materials, such as collagen, polymers, hydroxyapatite, calcium sulfate, ceramics, and bioresorbable polymers, among many others. It is understood that bone grafts can include those which have a predetermined shaped or which are comprised of smaller particles that can be formed into a desired shape at the time of implantation.

Regardless of the source, bone grafts must be adequately preserved for later implantation in a surgical setting. One common practice is to dehydrate the grafts by freeze-drying. This not only extends the shelf-life of the bone grafts, it also inhibits bacterial growth within the graft. Before implanting the graft into a recipient, however, the graft must be reconstituted or rehydrated with a suitable liquid. This can be done by immersing the bone graft in the liquid. The problem with this approach, however, is that infusion of the liquid through the pores of the graft is typically unacceptably slow for a surgical environment and does not ensure thorough and complete infusion of the liquid throughout the graft. Moreover, this approach increases the likelihood of exposing the graft to environmental pathogens.

Another significant challenge in preparing grafts for implantation is the uniform loading or seeding of grafts with desired biological components and cells. Developing functional tissue equivalents requires the effective and uniform seeding of biological components and cells into natural or synthetic matrices and allowing them to expand and develop into the tissue-like structure from the seeded cells. Thus, the ability to efficiently and uniformly seed biological components and cells into three-dimensional scaffolds remains a significant aspect in tissue engineering.

SUMMARY OF THE INVENTION

Methods and systems are disclosed herein for providing an improved apparatus and packaging system to more expeditiously reconstitute and hydrate medical grafts and to effectively and uniformly seed the medical grafts with biological components and cells.

In one preferred embodiment, a system for loading a biological solution into a porous substrate is provided. The system generally includes a container having an entry port, at least one substrate cavity, and top, side and bottom walls defining an inner surface of the container. The entry port is configured to receive the bone morphogenetic material. The cavity is in communication with the entry port and includes the porous substrate maintained under negative pressure. The container volume is substantially the same as a volume of the porous substrate.

In accordance with one aspect of the preferred embodiment, the bone morphogenetic material is selected from the group consisting of bone morphogenetic protein (BMP), transforming growth factor β (TGF-β), growth differentiation factor (GDF), and cartilage derived morphogenetic protein (CDMP).

In accordance with another aspect of the preferred embodiment, bone morphogenetic protein is selected from the group consisting of BMP-1, BMP-2, BMP-3, BMP-4, BMP-5, BMP-6, BMP-7, BMP-8, BMP-9, BMP-10, and BMP-11.

In accordance with yet another aspect of the preferred embodiment, the bone morphogenetic material is a recombinant human bone morphogenetic protein.

In accordance with a further aspect of the preferred embodiment, the recombinant human bone morphogenetic protein is rhBMP-2.

In accordance with yet a further aspect of the preferred embodiment, the porous substrate is a bioabsorbable absorbent matrix.

In another preferred embodiment, the absorbent matrix comprises a purified collagen matrix.

In accordance with one aspect of a preferred embodiment, the collagen may be Type I collagen, Type II collagen, Type IV collagen, cell-contracted collagen, or combinations thereof.

In accordance with another aspect of a preferred embodiment, collagen matrix comprises a nanofiber density of 10 nanofibers per 100 micron$^3$ collagen matrix volume.

In one preferred embodiment, a container for storing a resorbable osteoconductive matrix having a bioabsorbable absorbent matrix is provided. The container generally includes an internal cavity maintained under negative pressure, a receiving chamber configured to receive a biological solution and a storage chamber configured to store the resorbable osteoconductive matrix. The container also has a plurality of channels coupling the receiving chamber and the storage chamber together to disperse the distribution of the biological solution along a longitudinal length of the resorbable osteoconductive matrix at substantially the same time once the receiving chamber receives the biological solution.

In accordance with one aspect of a preferred embodiment, the collagen matrix has a nanofiber density of 10 nanofibers per 100 micron$^3$ collagen matrix volume.

In accordance with yet another aspect of a preferred embodiment, a method of rapidly binding a biological component to a medical implant prior to introduction into an individual is provided. The method may include providing a container with an internal cavity maintained under negative pressure that is configured to receive a biological component and a storage chamber configured to store a medical implant. The medical implant generally comprises a bioabsorbable absorbent matrix and a plurality of channels coupling the receiving chamber to the storage chamber which are configured to disperse the distribution of the biological component along a longitudinal length of the medical implant at substantially the same time once the receiving chamber receives the biological solution. A biological component is introduced into the receiving chamber of the container, wherein substantial binding is accomplished in less than 5 minutes.

In still other embodiments, the binding is accomplished in less than 2 minutes and preferably in less than 1 minute.

In some embodiments, substantial binding is greater than 50% binding of a biological component to an absorbent matrix and preferably greater than 75% binding of a biological component to an absorbent matrix.

Figure 1B:
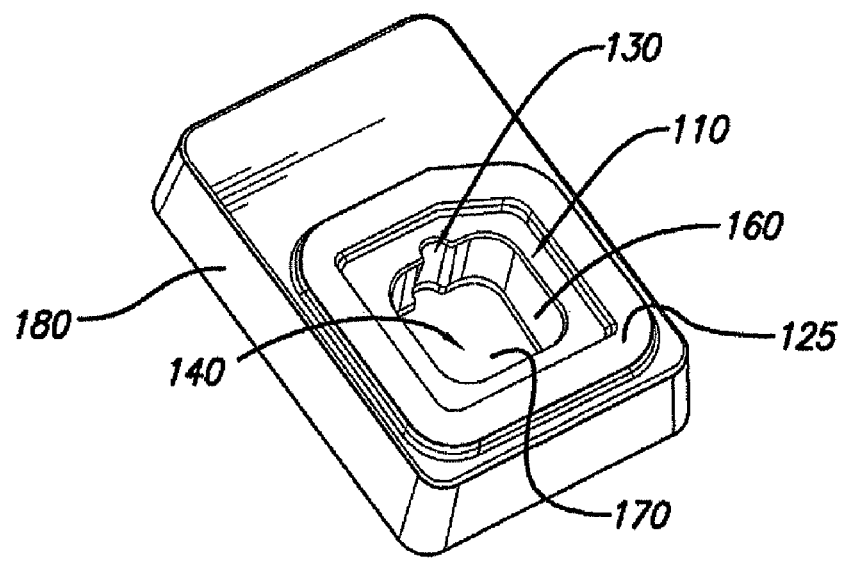
Figure 1C:
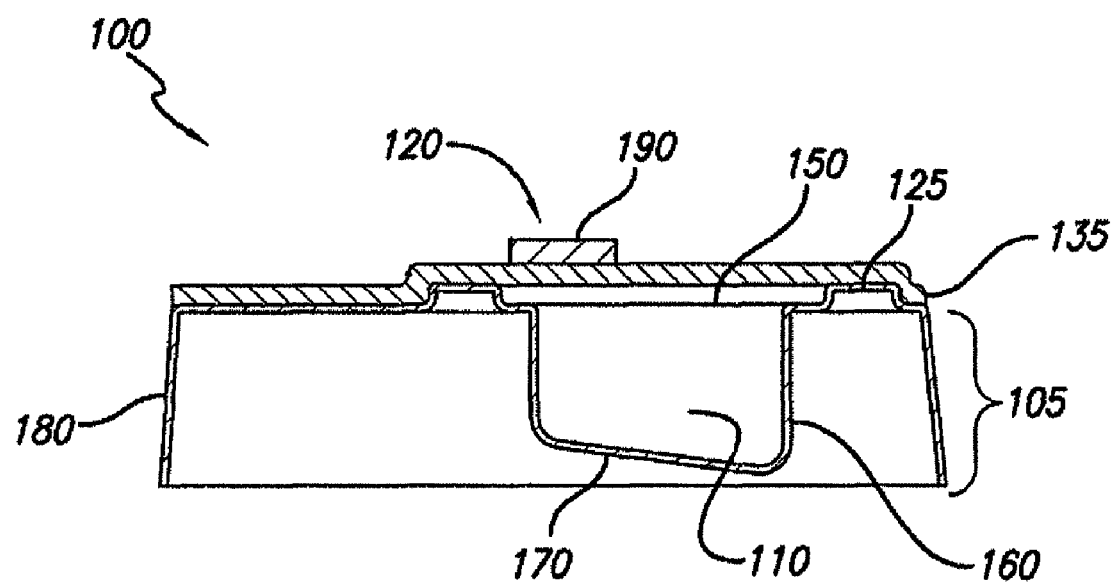

In yet other embodiments, a method of seeding bone morphogenetic material on a porous substrate is provided using a porous substrate in a container under negative pressure, wherein the container volume is substantially the same as a porous substrate volume. The method includes introducing a bone morphogenetic material to the porous substrate in a volume that does not exceed the porous substrate volume. Advantageously, the bone morphogenetic material is bone morphogenetic protein (BMP), transforming growth factor β (TGF-β), growth differentiation factor (GDF), or cartilage derived morphogenetic protein (CDMP). Optionally, the bone growth agent can be BMP-1, BMP-2, BMP-3, BMP-4, BMP-5, BMP-6, BMP-6, BMP-7, BMP-8, BMP-9, BMP-10, and/or BMP-11 and/or other suitable biological components and cells as described below in more detail.

In another preferred embodiment, a method of increasing binding of a biological agent to a medical implant is provided using a dehydrated bone medical graft implant in a container under negative pressure, where the container volume is substantially the same as the porous substrate volume and where the porous substrate is a bioabsorbable absorbent matrix. The absorbent matrix also includes a multiplicity of pores and substantially rigid nanofibers dispersed within the structure of the absorbent matrix. A biological solution is introduced to the dehydrated medical implant in a volume that does not substantially exceed the porous substrate volume and the negative pressure in the container produces a pressure differential that pushes the biological solution into the pores, thereby increasing the binding of the biological agent to the implant.

In still further embodiments, a method of mitigating migration of osteoinductive agents from a bone graft is provided using a bone graft in a container under negative pressure, where the container volume is substantially the same as a porous substrate volume and where the porous substrate includes a bioabsorbable absorbent matrix having a multiplicity of pores and substantially rigid nanofibers dispersed within the structure of the matrix. At least one osteoinductive agent is introduced to the bone graft in a volume that does not substantially exceed the porous substrate volume and the negative pressure in the container produces a pressure differential that binds the osteoinductive agent firmly to the graft. The graft is inserted into an individual in need thereof and the osteoinductive agent remains substantially within the porous substrate.

In other embodiments, a method of increasing uniform distribution of a biological solution on a bioabsorbable absorbent matrix is provided using a container comprising an entry port, at least one substrate cavity, and top, side and bottom walls defining an inner surface of the container where the entry port is configured to receive the biological material. The substrate cavity is in communication with the entry port and has the bioabsorbable absorbent matrix maintained under negative pressure. The container volume is substantially the same as the volume of the absorbent matrix. A biological solution is introduced into the entry port and a pressure differential is produced from the negative pressure, thereby forcing the solution into the plurality of pores of the bioabsorbable matrix.

Other objects, features and advantages of the present invention will become apparent to those skilled in the art from the following detailed description.

BRIEF DESCRIPTION OF THE DRAWINGS

FIG. 1A is a top perspective view of an embodiment of a medical implant container.

FIG. 1B is a top perspective view of the medical implant container of FIG. 1 without the lid.

FIG. 1C is a cross-sectional view of the medical implant container of FIG. 1A taken along the 1'-1' axis FIG. 2A is a front plan view of another embodiment of the medical implant container.

FIG. 2B is a rear perspective view of the medical implant container of FIG. 2A.

FIG. 3 is a top perspective view of a further embodiment of the medical implant container alongside a needle syringe.

FIG. 4A is a top perspective view of yet a further embodiment of the medical implant container.

FIG. 4B is a top perspective view of the medical implant container of FIG. 6A without the lid.

FIG. 5A is a top perspective view of yet a further embodiment of the of the medical implant container.

FIG. 5B is a top perspective view of the medical implant container of FIG. 5A showing substrate reconstitution using a syringe.

FIG. 6 is a data graph showing the relative binding strength of rhBMP-2 applied to Absorbable Collagen Sponges (ACS) contained in a vacuum sealed package (VIP).

FIG. 7 is a data graph showing the relative binding strength of rhBMP-2 applied to allograft bone tissue contained in a vacuum sealed package (VIP).

Like numerals refer to like parts throughout the several views of the drawings.

DETAILED DESCRIPTION OF EMBODIMENTS OF THE INVENTION

The present disclosure is directed to methods and systems for expeditiously reconstituting and hydrating medical grafts and for uniformly seeding medical grafts with biological components and cells. The methods and systems disclosed herein are particularly suited for surgical environments where the ability to quickly prepare grafts for implantation in a patient is desired. Although the present disclosure describes the methods and systems for hydrating medical grafts, particularly bone grafts, it is understood that the methods and systems can also be applied for a wide variety of medical and dental applications and also soft tissue applications, such as in regenerative medicine and tissue engineering. Accordingly, the term “graft” as used herein can be comprised of any naturally occurring tissue including bone tissue and soft tissues as well as any non-naturally occurring substance used as a graft, or any combination thereof.

FIGS. 1A-C depict various views of an embodiment of a medical implant system 100 that can be used in connection with the systems and methods disclosed herein. As shown in FIGS. 1A-C, the medical implant system 100 comprises container 110 that includes an entry port 120, a needle cavity 130 and a graft cavity 140 containing a medical implant, such as a dehydrated bone graft (not shown). As shown in FIG. 1A, a needle syringe can be inserted through the entry port 120 to deliver liquids, biological components, and/or cells into the needle cavity 130 and to the graft that is stored in the graft cavity 140 of the container 110. The needle cavity 130 is disposed adjacent the graft cavity 140 to receive the needle syringe and the liquids, biological components and/or cell.

It is desirable to maintain the entire container 110 under negative pressure and, more preferably, under substantial vacuum. This is because medical implants, such as bone grafts, are commonly dehydrated and freeze-dried for storage prior to use or implantation. The higher the negative pressure or vacuum within the container, the greater the evacuation of the pores within the graft and thus the greater infusion of the hydrating solution into the graft. Thus, it is preferable to have an absolute pressure inside the container as close to 0 mbar as possible. In a preferred embodiment, the absolute pressure inside the container is under 100 mbar, more preferably 10 mbar, and most preferably 1-5 mbar.

Freeze-drying involves a freezing process under negative pressure that results in a graft having low residual moisture. One advantage of this process is that it allows for storage of bone grafts and other biological material at room temperature. It also provides for increased shelf-life with reduced biochemical changes to the bone graft. Freeze-dried grafts thus offer the advantage of providing easy and economical storage prior to use.

In addition, it is preferable to reduce, if not completely eliminate, any residual moisture within the graft prior to packaging it in the container. This is because the negative pressure or vacuum in the container can cause the residual moisture to vaporize which, in turn, may cause the negative pressure or vacuum to decrease within the container. Preferably, the residual moisture within the graft is less than 6%, more preferably less than 3%, and most preferably 0%. A desiccant can be included in the container. The desiccant is preferably non-reactive with the graft or the solution that is used to hydrate the graft.

The bone graft is typically rehydrated or reconstituted with a saline solution prior to implantation in a patient or recipient. Rehydration of freeze-dried bone grafts typically involves soaking the grafts in the saline solution until the grafts reach the desired level of hydration. Depending on the size of the graft, among other factors, rehydration and reconstitution of a bone graft can take anywhere from one hour to a few days. Although it is desirable to achieve uniform penetration of the solution and homogenous rehydration of bone grafts, it is generally difficult to achieve these goals in the short period of time typically demanded in surgical environments.

The medical implant containers disclosed and described herein provide a means by which bone grafts, which have been freeze-dried or otherwise dehydrated, can be expeditiously and uniformly hydrated and reconstituted prior to implantation. Because the medical implant containers substantially maintain the negative pressure during the hydration/reconstitution of the graft, the time for hydration or reconstitution is substantially reduced. The penetration of solution into the implant is enhanced by the vacuum induced suction effect. The negative pressure produces a pressure differential that pushes the solution into the interstice or pores of the implant. Once the solution is distributed into the pores, it can be further distributed throughout the implant via capillary action.

In one embodiment, the medical implant vacuum infused package container system provides substantial hydration and reconstitution, along with substantially uniform seeding and loading of biological components and cells, within one hour from infusion. In other embodiments, the medical implant and vacuum infused package container system provides substantial hydration and reconstitution, along with substantially uniform seeding and loading of biological components and cells, within 30 minutes from infusion. In still other embodiments, the medical implant and vacuum infused package container system provides substantial hydration and reconstitution, along with substantially uniform seeding and loading of biological components and cells, within 20 minutes from infusion. In yet other embodiments, the medical implant and vacuum infused package container system provides substantial hydration and reconstitution, along with substantially uniform seeding and loading of biological components and cells, within 15, 14, 13, 12, 11, 10, 9, 8, 7, or 6 minutes from infusion. In further embodiments, the medical implant and vacuum infused package container system provides substantial hydration and reconstitution, along with substantially uniform seeding and loading of biological components and cells, within 5 minutes or less from infusion, including 4, 3 or 2 minutes and preferably less than or equal to 1 minute.

Even when uniform loading or seeding of grafts is obtainable, the next challenge is assuring that the biological components and cells can bind to the graft in such a manner that they do not improperly precipitate out of the graft once inside the patient's body. For example, premature or excessive precipitation of Bone Morphogenetic Protein (BMP) from the graft implant into surrounding tissue has been known to stimulate bone formation in undesirable locations. Under these conditions, ectopic bone growth has been observed in muscle tissue surrounding the implant and in more serious cases, involving implants in the cervical spinal area, ectopic bone growth has been known to completely surround the subject's trachea closing off their air passage and causing suffocation. Accordingly, it is desirable to maximize the ability of biological components and cells to bind with the graft implant in order to avoid their excessive or premature precipitation into surrounding tissue.

In one embodiment, a method of rapidly and substantially binding a biological component to an implant is provided. As used herein, the term "rapidly" is meant to compare the shortened binding time of a biological component to an implant using the disclosed vacuum infusion package container with the binding time of prior art infusion systems. Prior art infusion systems are disclosed, for example, by W. Friess et al. in "Characterization of absorbable collagen sponges as rhMBP-2 carriers" International Journal of Pharmaceutics 187 (1999): pages 91-99, the contents of which are hereby incorporated by reference in their entirety, especially with regard to the binding properties of rhMBP-2 to absorbable collagen sponges. In a preferred embodiment, the biological component is bound to the implant in less than fifteen minutes from the time it is introduced into the vacuum infusion package container having a porous substrate disposed therein. More preferably, rapid binding is accomplished in less than 10, less than 9, less than 8, less than 7, less than 6, less than 5, less than 4, less than 3, or less than 2 minutes from the time the biological component is introduced into the disclosed system. In a particularly preferred embodiment, the biological component is bound to the porous substrate in less than one minute. The term "substantially", as used herein, refers to at least fifty percent of the biological component being bound to the implant. In a preferred embodiment, "substantially bound" or "substantially binding" refers to at least 60%, 65%, 70%, 75%, or 80% binding of the biological component to the implant. In a particularly preferred embodiment, 85% of the biological component is bound to the implant.

In FIGS. 1A-C, since the entire container 110 is maintained under negative pressure or vacuum, it is desirable to reduce the internal volume of the container 110 to the extent necessary to house the bone graft. This is because it is generally more difficult to maintain negative pressure or a vacuum for larger volumes of space. In a preferred embodiment, the volume of the container is substantially the same as the volume of the graft. In accordance with one aspect of this preferred embodiment, the volume of the container is no greater than approximately 125%, preferably no greater than approximately 110%, and more preferably no greater than 105%, of the volume of the graft. In accordance with another aspect of this preferred embodiment, the volume of the container is equal to the volume of the graft. As shown in FIGS. 1A-C, the interior volume of the container 110 is bounded by top 150, side 160 and bottom 170 walls. A septum 190 is coupled to the entry port 120 and disposed externally of the container 110 so as to reduce an internal volume of the container 110 required to accommodate the septum. The materials selected for the container are preferably characterized as having high gas barrier properties to ensure that the negative pressure or vacuum is effectively maintained over time.

Figure 4A:
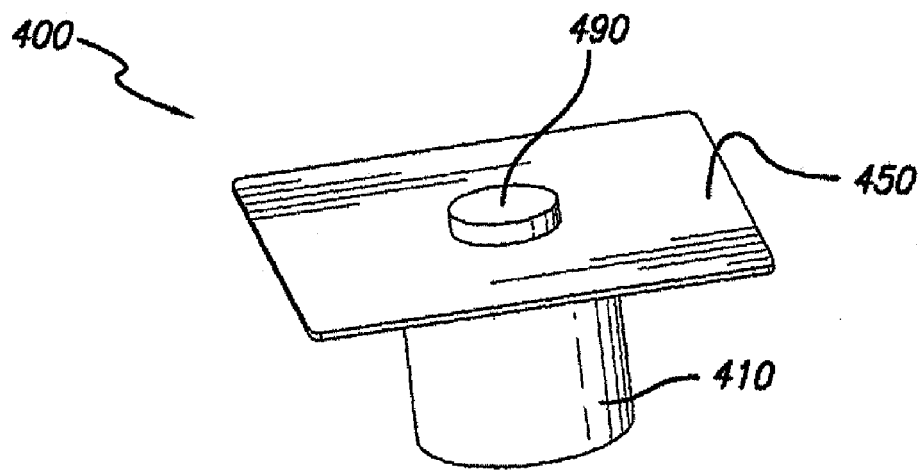
Figure 4B:
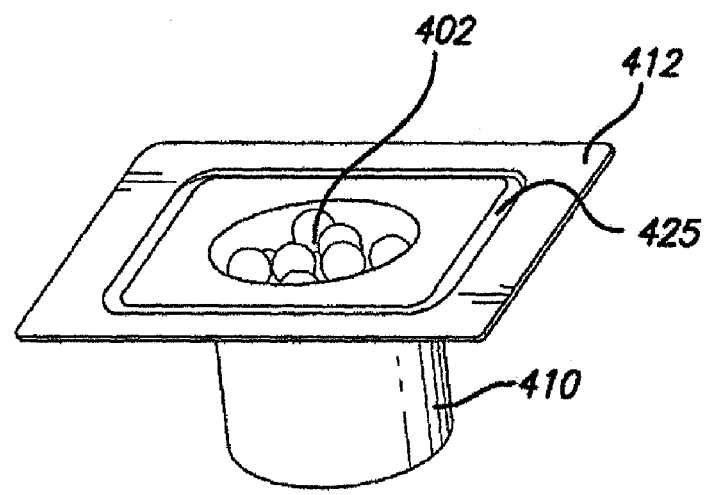

Other embodiments of the medical implant containers can be similarly designed to reduce the internal volume that is maintained under negative pressure. For example, FIGS. 4A-B depicts a medical implant container 400 comprising bone graft chips 402 contained within a graft cavity 410. A lid 450 is hermetically sealed to the peripheral lip 412 of the graft cavity 410 by a heat weld 425. As can be seen in FIGS. 4A-B, the bone graft chips 402 fill the graft cavity 410 to near capacity such that the volume of the graft cavity 410 is substantially the same as the volume of the bone graft chips 402. A septum 490 is disposed externally of the graft cavity 410. Preferably, the septum is self-sealing after puncture with a needle syringe delivering the hydrating solution to the graft chips 402 so as to sustain the negative pressure/vacuum inside the graft cavity 410.

Referring back to FIGS. 1A-C, the medical implant system 100 further comprises support members 180 to support the container 110 in a substantially stable and upright position. This will permit the surgeon to place the system 100 on a flat surface and simply insert a needle syringe into the entry port 120 with a single hand without having to support the system 100 with the other hand in the desired upright position. Although FIGS. 1A-C show the support members 180 as a single peripheral wall that surrounds the container 110, it is understood that the structure of the support members 180 is not so limited and can include other structures capable of stabilizing the container 110 in a sufficiently stable position to permit the surgeon to perform the injection step into the entry port 120.

The system 100 is shown to generally comprise a bottom portion 105 and a lid portion 135. The bottom portion 105 and the lid portion 135 can be hermetically-sealed by welding the two portions together so that a negative pressure can be maintained inside the container 110. It is preferable to position the weld as close to the periphery of the container 110 so as to further reduce the amount of dead airspace that may remain between the bottom portion 105 and the lid portion 135. The resulting weld 125 can surround the entire periphery of container 110. Although the system 100 depicted in FIGS. 1A-C is shown as a two-part structure comprising a bottom portion 105 and a lid 135, it is understood that the container can be constructed as an integral structure, such as an elastic vacuum package.

In addition to expeditious and uniform hydrating or reconstituting bone grafts, the system 100 promotes the efficient and uniform distribution and seeding of biological components and cells into the pores of the grafts. Biological components and cells can be delivered to the grafts in solution via needle syringe having the appropriate gauge so as to ensure against structural or cellular damage as they are passed through the needle syringe.

Generally, there are three ways in which a graft can help repair a bone defect. The first is called osteogenesis, the formation of new bone by the cells contained within the graft. The second is osteoinduction, a chemical process in which molecules contained within the graft, such as bone morphogenetic proteins, convert the patient's cells into cells that are capable of forming bone. The third is osteoconduction, a physical effect by which the graft forms a scaffold onto which cells in the recipient are able to colonize and form new bone. Thus, the methods and systems disclosed herein provide for preparing bone grafts to include biological components and cells to help repair a bone defect in the recipient.

The interior surface of the container 110 is preferably configured to help preserve the integrity of the biological components and the cells during delivery to the bone graft. Particularly, the needle cavity 130 and the side 160 and bottom 170 walls are configured to promote a laminar flow of the biological solution received through the entry port. A laminar flow is characterized either as smooth or non-turbulent fluid flow. It is preferable to promote a laminar flow, and therefore reduce a turbulent flow, of the biological solution in the container 110 so as to preserve the structural and cellular integrity of the biological components and cells contained in the solution. A turbulent flow can, for example, cause the cells to become lysed and clump together. Eliminating, or at least reducing, sharp edges, corners or angles within the container 110 which the biological solution can come into contact with in the container can help promote a laminar flow of the solution. It is noted that because the liquid is expelled into the needle cavity and towards the bottom surface 170 of the container 110, the configuration of the top wall or lid portion 105 of the container 110 or where the side walls 160 meet the lid portion 105 of the container 110 are not as critical and therefore do not necessarily need to be curved.

As can be seen in FIGS. 1B-C, the side 160 and bottom 170 walls of the container 110 converge together as curved surfaces having radii of curvature greater than zero. Moreover, the internal surface of the needle cavity 130 is also provided as a curved surface having a radius of curvature greater than zero. Additionally, as shown in one embodiment depicted in FIG. 1C, the bottom wall 170 is angled downward from the entry port 120 and the needle cavity 130 so as to ensure that the biological solution flows across and is distributed along a bottom length of the graft. This not only ensures the uniform distribution of the solution throughout the graft, it also prevents the pooling and waste of the solution in the needle cavity 130. Thus, embodiments of the medical implant container further provide for substantially precise dosing of a quantity of biological components or cells to be introduced. However, it is to be understood that in other embodiments, the bottom wall 170 need not be angled downward from the entry port 120 and the needle cavity 130.

Figure 2A:
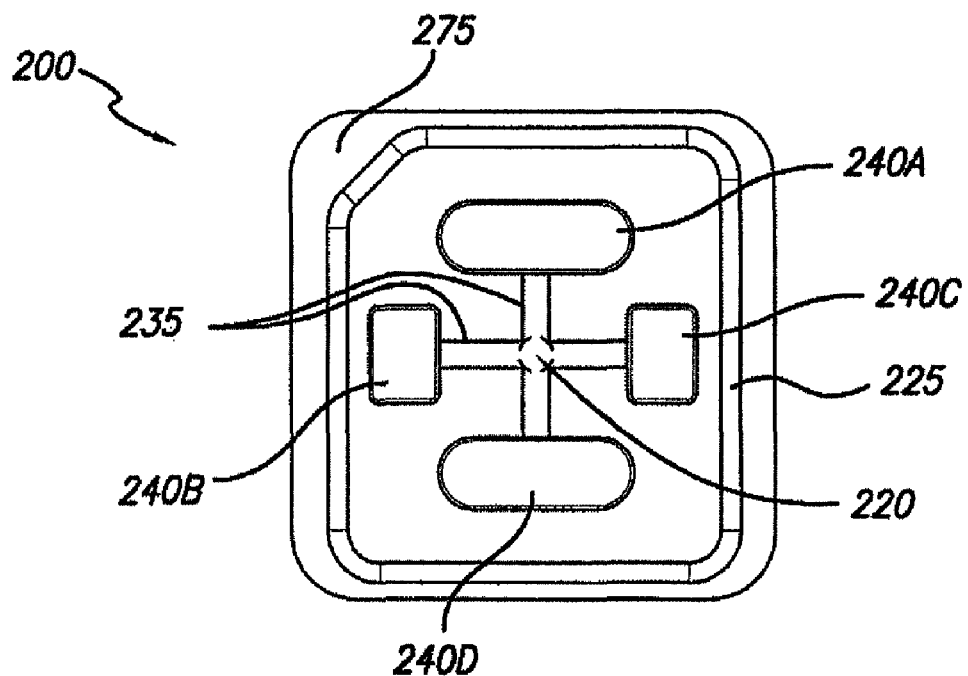
Figure 2B:
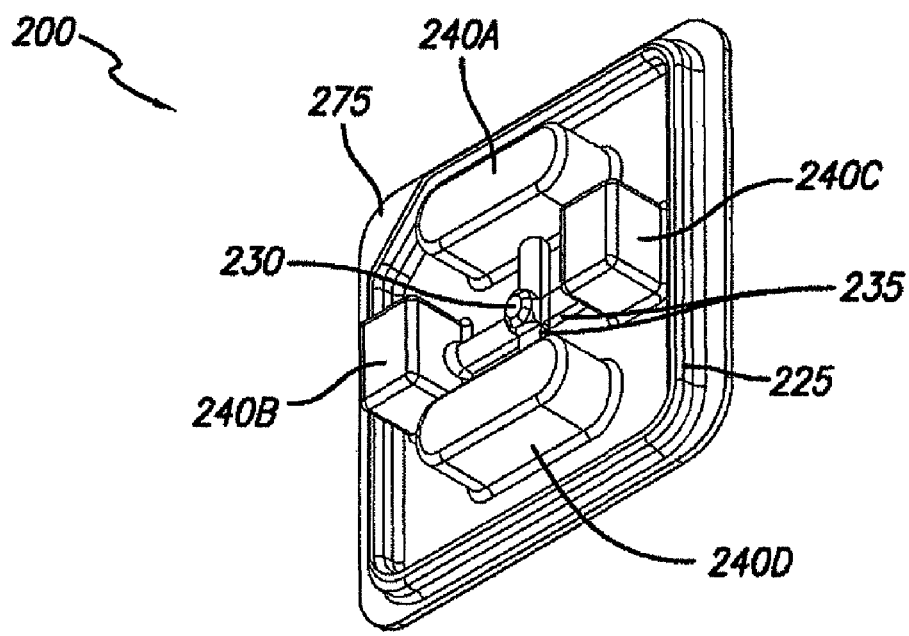

Alternate embodiments provide an efficient way to hydrate or reconstitute more than a single bone graft at the same time. FIGS. 2A-B show an embodiment of the medical graft container 200 comprising a single entry port 220 and a corresponding needle cavity 230 and a plurality of graft cavities 240A, 240B, 240C, and 240D coupled to and in fluid communication with the needle cavity 230 via channels 235. Once the grafts are loaded into the graft cavities 240A, 240B, 240C, and 240D, a gas communication is applied to the container so as to evacuate air remaining in the graft cavities. The container 200 can comprise a bottom portion and a lid that is optionally hermetically-sealed by a weld 225. A peripheral lip area 275 can be provided wherein the lid portion can be pulled apart from the bottom portion to open the container 200 and remove the bone grafts.

Developing functional tissue equivalents requires the effective and uniform seeding of biological components and cells into natural or synthetic matrices and allowing them to expand and develop into the tissue-like structure from the seeded cells. Thus, the ability to efficiently and uniformly seed biological components and cells into three-dimensional scaffolds remains highly desirable.

Figure 3:
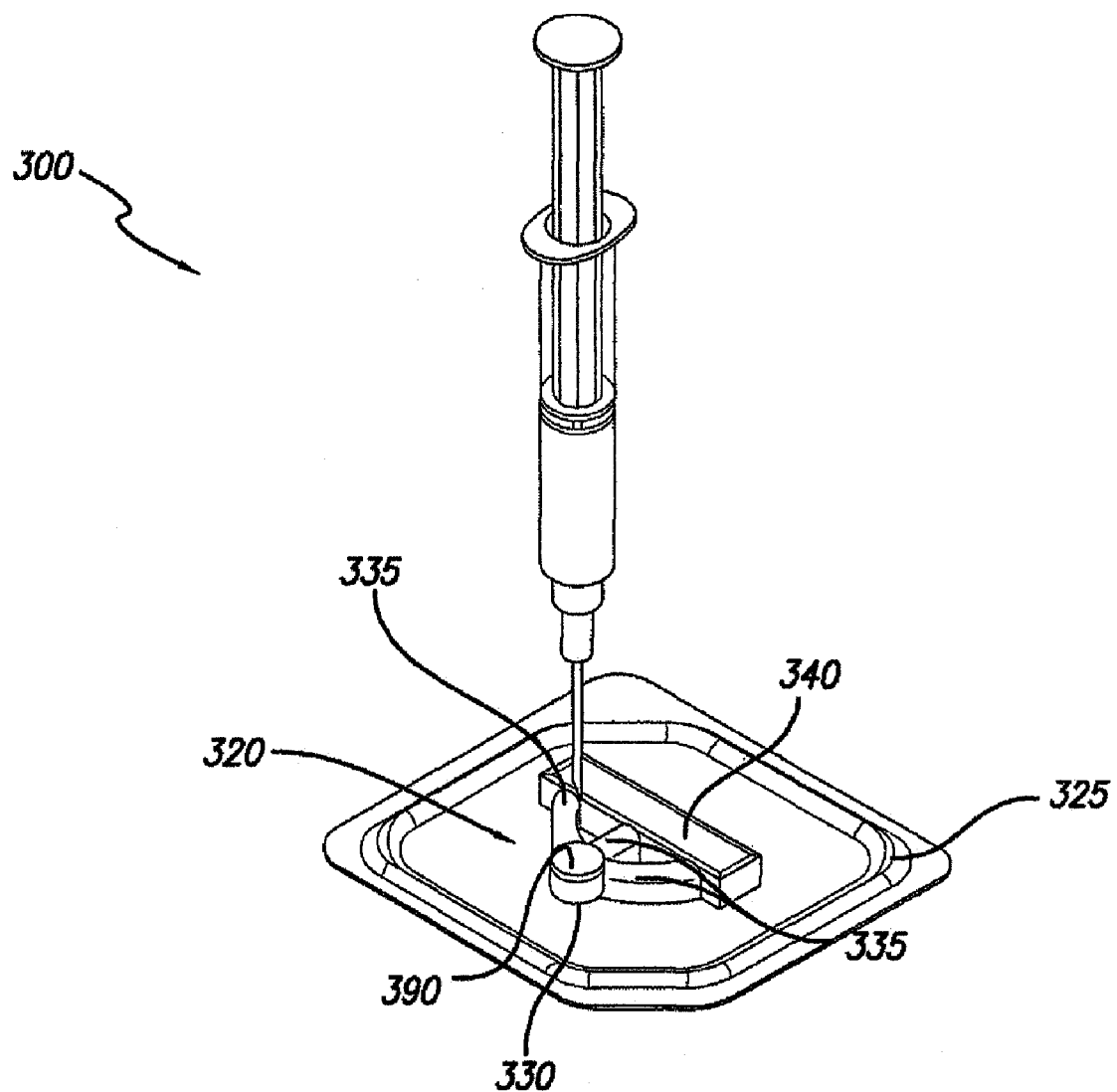

FIG. 3 depicts yet another embodiment of the medical graft container 300 alongside a needle syringe. The container 300 is designed to disperse the distribution of desired biological components and cells by providing a plurality of delivery channels 335 along a length of the graft cavity 340. The graft cavity 340 is preferably molded to the precise dimensions and shape of the dehydrated bone graft. The biological components and cells can be delivered via needle syringe through entry port 320 and into the needle cavity 330. A negative pressure or vacuum is maintained in the needle cavity 330, the delivery channels 335, and graft cavity 340. A septum 390 can optionally be coupled to the entry port 320 to maintain the negative pressure or vacuum after puncture with the needle syringe. The container 300 can be hermetically sealed by a weld 325 peripherally of the needle cavity 330, delivery channels 335 and graft cavity 340.

Figure 5A:
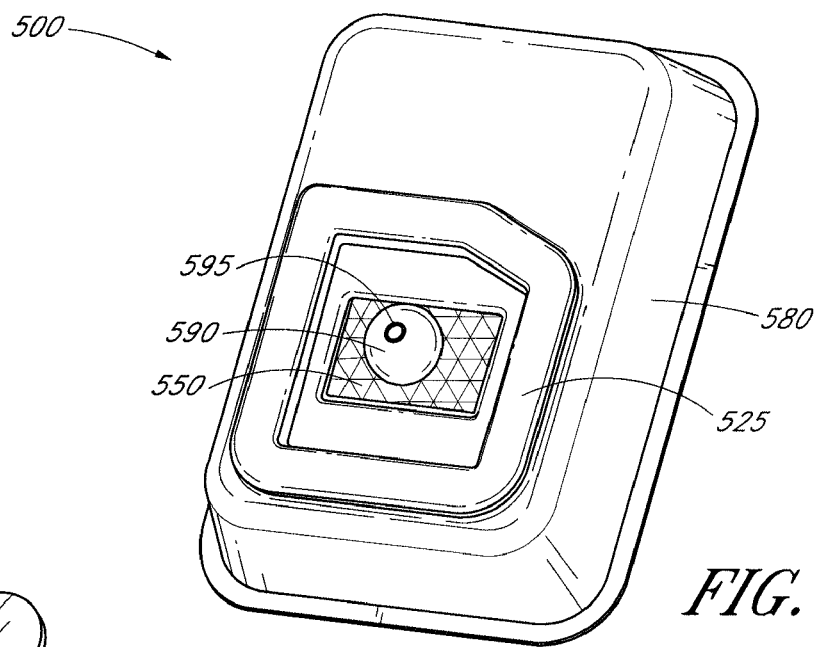
Figure 5B:
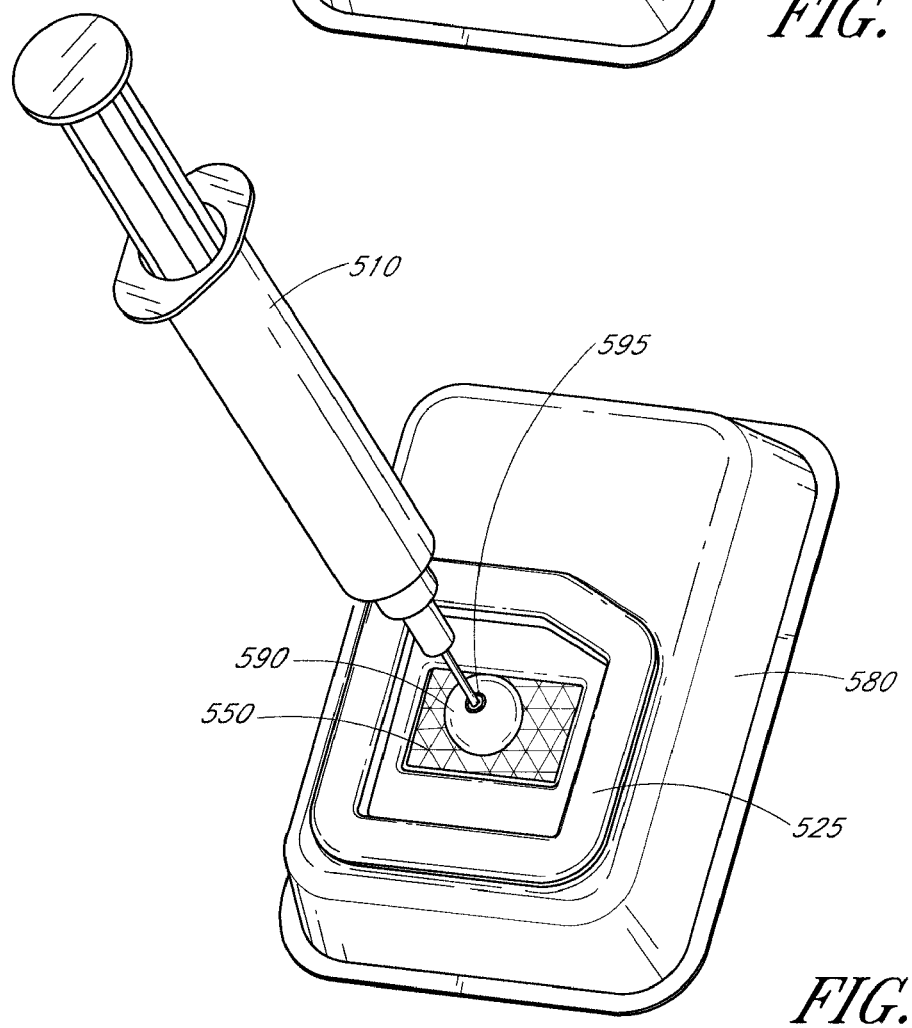

FIG. 5A depicts yet another embodiment of a medical graft container 500. FIG. 5B illustrates how a medical graft disposed within the medical graft container 500 of FIG. 5A can be infused with a suitable aqueous composition utilizing needle syringe 510. The container 500 is designed to disperse the distribution of desired biological components and cells from a distance closer to the middle of the medical graft by providing a septum 590 above the medical graft disposed within the graft cavity 550. This can be especially desirable for medical grafts that resist diffusion of the aqueous composition due to small pore size or other factors influencing the diffusion characteristics of the medical graft, such as viscosity of the aqueous composition. The medical graft container 500 can also be used in cases where it is desirable to set up a concentration gradient of the biological components or cells within a medical graft having a higher concentration of biological components and cells closer to the middle of the medical graft and a lower concentration of biological components and cells further away from the middle of the medical graft. The needle syringe 510 is inserted into the medical graft during infusion of the aqueous composition, or the needle syringe is merely placed above or adjacent to the medical graft during infusion. The graft cavity 550 is preferably molded to the precise dimensions and shape of the medical graft. The biological components and cells can be delivered via needle syringe through entry port 595 of septum 590 to the medical graft disposed within the graft cavity 550. The container 500 can be hermetically sealed by a weld 525 peripheral to the graft cavity 550 and support members 580 can be provided to support the container 500 in a substantially stable and upright position.

The aqueous compositions used herein to hydrate or reconstitute the bone grafts prior to implantation can be solutions, emulsions, micro-emulsions, suspensions or combinations thereof. Materials that function as emulsifiers or suspension aids can also be present in such aqueous compositions. Non-limiting examples of such emulsifiers or suspension aids include cell growth mediums, serums, differentiation mediums, nutritional mediums, monoglycerides, esters of monoglycerides, diglycerides, esters of diglycerides, polyglycerol esters of fatty acids, propylene glycol esters of fatty acids, sorbitan stearates, stearoyl lactates, lecithins, phospholipids, glycolipids, cellulose esters, gellan, pectin, xanthan, rhamsam and gum arabic.

In some embodiments, the aqueous compositions further contain water-miscible biocompatible solvents or solvent mixtures. The biocompatible solvents are preferably organic liquids in which the grafts are at least partly soluble at mammalian body temperatures and is substantially non-toxic in the quantities used. By way of example and not limitation, suitable water-miscible biocompatible solvents include ethanol, acetone, and dimethylsulfoxide as well as other suitable water-miscible biocompatible solvents.

Biological components used in connection with the medical implants disclosed herein include any agent that produces a biological, therapeutic or pharmacological result in a human. Exemplary biological components include, for example, any transforming growth factor $\beta$ (TGF-$\beta$), growth differentiation factor (GDF), and cartilage derived morphogenetic proteins (CDMP); any bone morphogenetic proteins (BMPs) including but not limited to BMP-1, BMP-2, BMP-3, BMP-4, BMP-5, BMP-6, BMP-6, BMP-7, BMP-8, BMP-9, BMP-10, and BMP-11; angiogenic factors; growth factors; hormones; anticoagulants, such as heparin and chondroitin sulphate; fibrinolytics, such as tPA; amino acids; peptides and proteins, including synthetic peptides and proteins, and including enzymes such as streptokinase, urokinase and elastase; steroidal and non-steroidal anti-inflammatory agents, such as hydrocortisone, dexamethasone, prednisolone, methylprednisolone, promethazine, aspirin, ibuprofen, indomethacin, ketorolac, meclofenamate, tolmetin; calcium channel blockers, such as diltiazem, nifedipine, verapamil; antioxidants such as ascorbic acid, carotenes and alpha-tocopherol, allopurinol, trimetazidine; antibiotics, such as gentamicin, noxythiolin and other antibiotics to prevent infection; prokinetic agents to promote bowel motility, agents to prevent collagen crosslinking such as cis-hydroxyproline and D-penicillamine; anti-cancer agents; neurotransmitters; hormones; immunological agents including elemetals and antibodies; nucleic acids including antisense agents; fertility drugs, psychoactive drugs; and local anesthetics, among numerous additional agents.

One group of biological components that are particularly useful in conjunction with bone grafts are Bone Morphogenetic Proteins (BMPs). BMPs are a group of growth factors and cytokines known for their ability to induce the formation of bone and cartilage. Currently, there are about twenty known BMPs including for example BMP-1, BMP-2, BMP-3, BMP-4, BMP-5, BMP-6, BMP-6, BMP-7, BMP-8, BMP-9, BMP-10, and BMP-11. BMP-2 and BMP-7 are a well know and used BMPs belonging to the Transforming Growth Factor beta (TGF-$\beta$) super family of proteins, a large family of structurally related cell regulatory proteins. BMP-2 and BMP-7 are osteogenic BMPs that potently induce osteoblast differentiation in a variety of cell types. BMPs, used in conjunction with the medical grafts described herein, can be derived from animals, humans (hBMP) or through recombinant DNA techniques (rhBMP). One particularly well known BMP currently utilized in bone grafts is rhBMP-2, also known as Dibotermin Alfa. rhBMP-2 can be efficiently manufactured using recombinant DNA techniques that genetically engineer or manipulate cells, bacteria, or yeast to produce rhBMP-2 in large quantities, as is well understood in the art. Examples of using BMPs in bone grafts is described in US Patent Application Publication No. 2004/0230310 A1 entitled, "USE OF MORPHOGENETIC PROTEINS TO TREAT HUMAN DISC DISEASE," which is herein incorporated by reference in its entirety.

The methods and systems disclosed herein can also be utilized to deliver living cells to desired sites in a recipient. Examples of such cells include but are not limited to stem cells, bone marrow derived stem cells, adipose derived stem cells, bone marrow stromal cells, bone cells, hepatocytes, keratinocytes, chondrocytes, osteocytes, osteoblasts, osteoclasts, mesenchymal stem cells, fibroblasts, muscle cells, parenchymal cells, cells of intestinal origin, nerve cells, skin cells, endothelial cells, epithelial cells, and smooth muscle cells. These cells may be cultured, differentiated, or expanded prior to seeding. These cells can be concentrated prior to implantation by methods such as centrifugation or filtration. Thus, the medical implants seeded can function as adhesion substrates, anchoring cells to be transplanted to effect the survival, growth and ultimately, grafting or anchoring of the transplanted cells to normal cellular tissue.

Other useful cell types include bone marrow derived stem cells, adipose derived stem cells, bone marrow stromal cells, chondrocytes, osteocytes, osteoblasts, osteoclasts, mesenchymal stem cells, fibroblasts, muscle cells, hepatocytes, parenchymal cells, cells of intestinal origin, nerve cells, and skin cells, and be provided as primary tissue explants, preparations of primary tissue explants, isolated cells, cell lines, trans formed cell lines, and host cells. The implants also include additional components such as biologically active agents or factors that alter the characteristics, such as osteoinductivity, metabolic agents, resorbability, strength, adherence, injectability, and frictional characteristics.

Immune responses to cortical bone grafts and other substrates (e.g., cement, IPN, etc.) are minimized while improving osteoinductive potential by modifying the grafts to have an osteoinductive surface that the recipient's body will accept as its own tissue type and therefore will not reject it or otherwise cause to fail. Such a process provides for the osteoinductive surface modification to be achieved via seeding of the surface of a porous graft substrate with periosteal cells that have been previously harvested either from the graft recipient or from an allogenic or xenogenic donor source.

Porous substrates which can be used in connection with the disclosed methods and systems include autograft, allograft, xenograft, or other non-human animal-based materials such as collagen and other peptide comprising implants. Synthetic materials including ceramics, hydroxyapatite, bioresorbable polymers and the like can also be used as graft materials. In some embodiments, the porous substrate is an osteoconductive matrix comprising a biologically acceptable matrix sponge. The sponge is preferably a collagen sponge as will be described in greater detail below.

In certain embodiments, the pore size of the grafts can be configured to accommodate the dimensions of the biological components and cells that are to be distributed or seeded into the grafts. The pore size is optimally configured to accommodate the viscosity of aqueous compositions which are used to hydrate and/or reconstitute the grafts. The high viscosity of certain aqueous compositions may be due to the inclusion of proteins and other high molecular weight biomolecues. Thus, the consideration of scaffold pore size, density, and porosity can be configured to influence the behavior and quality of the regenerated tissue. The pore size for bone regeneration is preferably about 100 to about 600 microns.

Synthetic polymers suitable for use in synthetic grafts include, but are not limited to: polyhydroxybutyrate (PHB); poly-n-vinyl pyrrolidone; polyorthoesters; polyanhydrides; polycyanoacrylates; polydepsipeptides; polydihydropyrans; poly-DL-lactide (PDLLA); polyesteramides; polyesters of oxalic acid; polyglycolide (PGA); polylactide-co-glycolide (DLPLG); polyetheretherketone (PEEK); polyetherketoneketone (PEKK); polyiminocarbonates; polylactides (PLA); polyorthoesters; poly-p-dioxanone (PDO); polypeptides; polyphosphazenes; polysaccharides; polyurethanes (PU); polyvinyl alcohol (PVA); poly-β-hydroxypropionate (PHPA); poly-β-hydroxybutyrate (PBA); poly-γ-valerolactone; poly-β-alkanoic acids; poly-β-malic acid (PMLA); poly-ε-caprolactone (PCL); and trimethylene carbonate (TMC), to name a few.

In some embodiments, the synthetic substrates include polymers that are biostable, while in other embodiments, the synthetic substrates include polymers that are bioresorbable. Suitable inorganic substrates include various types of natural and non-naturally occurring calcium phosphates, such as tricalcium phosphate, hydroxy apatite, poorly crystalline apatite calcium phosphate (PCA), amorphous calcium phosphate (ACP). As the main inorganic component of bone consists of a highly substituted calcium phosphate (CaP) apatite, synthetic bone substitutes comprising the various forms of CaP are particularly useful. Such CaP based materials include hydroxyapatite, carbonated apatite, fluoroapatite, alpha- and beta-tricalcium phosphate, tetracalcium phosphate, octacalcium phosphate, and combinations thereof. The materials are preferably configured to have an appropriate level of porosity, pore size, and size of the interconnections between pores.

In one embodiment, the porous substrate is a bioabsorbable absorbent matrix. Preferably, the bioabsorbable absorbent matrix is absorbent, flexible, malleable, compressible, porous, bioresorbable and biocompatible. One example of a suitable absorbent matrix is an Absorbable Collagen Sponge (ACS) as is taught in U.S. Patent Application Publication No. 2007/0142916 A1 entitled "BONE GRAFT COMPOSITION, METHOD AND IMPLANT," which is herein incorporated by reference in its entirety.

In a preferred embodiment, the absorbent matrix is derived from Type I bovine tendon collagen, given that animal type I collagen is homologous to human type I collagen. However, other fibril forming collagen such as types II, III, V and XI and physiologically compatible collagen obtained from transgenic animals, or any combination thereof, can be used either singularly or in combination with type I collagen to form the absorbent matrix. After harvesting, the tendon is treated with alkali solutions and the extracted collagen can be cross-linked with heat or a suitable chemical cross-linking agent (aldehyde, DHT, UV, etc.) to become a sponge like material that is particularly suitable as a resorbable collagen sponge. After the collagen is formed into a sponge, the material is sterilized using a suitable chemical or method, such as ethylene oxide, ethanol, etc. The collagen matrix preferably has pores of a sufficient size and quantity to permit growing tissue to infiltrate therein. The pore size preferably ranges from about 10 μm to about 500 μm, more preferably from about 50 μm to about 150 μm with surface pores being smaller than cross-sectional (internal) pores. In particularly preferred embodiments, the surface pores range in diameter from about 30 μm to about 150 μm, with about 70 μm being most preferred. Cross-sectional pores can range in diameter from about 50 μm to about 300 μm, with about 150 μm being most preferred. A preferred form of the resorbable osteoconductive matrix is describable as an homogeneous biologically compatible porous matrix having a isopycnic density with a liquid growth medium, a sponge-like character and diameters of less than about 2 millimeters, each particle having a multiplicity of voids, the voids representing at least 10 percent of the total volume of the matrix, the voids being connected to pores of less than 100 micrometers in diameter, which connect the voids to the exterior of the matrix. The collagen matrix can also comprise a multiplicity of substantially rigid nanofibers dispersed within the collagen matrix to impart structural integrity to the collagen matrix with nanofiber ends projecting out of a surface of the collagen matrix to provide differential load bearing surface bristles.

In this application, the term "substantially rigid" means substantially devoid of flexibility in the environment used. Rigidity can be measured by the modulus of elasticity in shear. In this aspect, "substantially rigid" can mean a nanofiber with a modulus of elasticity between 4.2 MPa and 15.0 MPa, desirably between 6.0 MPa and 14.0 MPa and preferably between 9.0 MPa and 12.0 MPa, with the higher MPa values obtainable by cross-linking.

The term "nanofiber" means an elongated nanostructure having one principal axis that is longer than the other two principal axes and an aspect ratio greater than one or greater than 10 or greater than 500. A shorter axis can be less than 100 nm, or less than 10 nm or less than 5 nm. The nanofiber can have a substantially uniform diameter. The diameter can show a variance less than 20%, less than 5%, or less than 1% over the region of greatest variability. Typically the diameter is evaluated away from the ends of the nanofiber over a central 20%, 50% or 80% of the nanofiber. In other embodiments, the nanofiber has a non-uniform diameter, varying in diameter along length. Also in certain embodiments, the nanofiber can be substantially crystalline and/or substantially monocrystalline.

"Nanofiber" includes such structures as nanowires, nanowhiskers, semi-conducting nanofibers, carbon nanotubes and composite nanotubes so long as they impart a bristled surface to the resorbable osteoconductive matrix of the invention. The nanofiber can comprise any number of materials, based on certain factors, including intended use of the bristled surface, conditions of use such as temperature, pH, light such as UV sensitivity, placement environment, reactions to be supported by the resorbable osteoconductive matrix, required surface durability and even cost. Ductility and breaking strength of the nanofibers can vary depending on composition. For example, ceramic ZnO nanofiber wires can be more brittle than silicon or glass nanowires, while carbon nanofiber tubes may have a higher tensile strength.

Although collagen is a good example of a rigid nanofiber, other polymers are suitable as well. Derivatives of other biopolymers that are rod-like, such as tubulin and keratin that can be manufactured in rigid nanofiber form can be suitable so long as they retain a fiber structure integrity under conditions of matrix formation. A preferred nanofiber is a nanometer scale rod-like polymer that is water compatible and has polar surface groups such as amino groups.

Other nanofibers for applications of the resorbable osteoconductive matrix include silicon, ZnO, TiO, carbon, carbon nanotubes, glass, and quartz. The nanofibers disclosed herein can be coated or functionalized to enhance or add properties. Polymers, ceramics or small molecules can be used as coating materials. The coatings can impart characteristics such as water resistance, improved mechanical or electrical properties or specificities for certain analytes. Additionally, specific moieties or functional groups can be attached to or associated with the nanofibers.

In one embodiment, the nanofiber is formed by methylated collagen. This material has a relatively high (above 25° C.) glass transition temperature that imparts improved structural integrity and surface bristling to the resorbable osteoconductive matrix.

Different applications of the invention will require different densities of nanofibers per unit volume of osteoconductive matrix. In some exemplary applications, the number of nanofibers per unit volume is 1 nanofiber per 10 micron$^3$ to 200 nanofibers per micron$^3$ volume matrix or from 10 nanofibers per micron$^3$ to 100 nanofibers per micron$^3$; or from 25 nanofibers per micron$^3$ to 75 nanofibers per micron$^3$ volume matrix. In other nanowire embodiments, a density can range from about 1 to 3 nanowires per cubic micron to 2,500 nanowires per cubic micron of matrix.

An overall area of a nanofiber can be increased by increasing thickness or diameter. The diameter can be controlled through choice of composition, growth conditions, moieties or coatings. A preferred nanofiber thickness is between 5 nm to 1 micron; from 10 nm to 750 nanometers or from 75 nm to 100 nanometers.

In addition to diameter, surface area of nanofibers and correspondingly the bristled surface area of resorbable osteoconductive matrix are influenced by length of the nanofibers. For some fiber materials, increasing length results in increasing fragility. Accordingly, preferred fiber lengths will be between 2 microns and 1 mm; between 10 microns to 500 micrometers; or between 50 microns to 100 microns. Some embodiments of the invention have nanofibers of approximately 40 nm in diameter and approximately 50 microns in length.

The nanofibers can be substantially homogeneous in material properties or they can be heterogeneous. They can be fabricated from any convenient material or materials. The nanofibers can comprise "pure" materials, substantially pure materials and doped materials. They can include insulators, conductors or semiconductors. The nanofiber material can vary depending upon specific functionalization such as durability, cost or condition of use. The nanofiber material can be the same as the resorbable osteoconductive matrix material or the nanofiber material can be different from the matrix.

Producing the Matrix with Dispersed Nanofiber

The resorbable osteoconductive matrix comprises dispersed fibers, some of which have ends that are elevated above the matrix surface in a bristled pattern. In one embodiment, the matrix has at least a portion of dispersed nanofibers that have ends that are elevated at least 10 nm, and in other embodiments at least 100 nm above the matrix surface. A preferred bone regenerative composition comprises bristled nanofiber ends extending between 40 nm and 100 nm above a collagen matrix surface. The bristles form a complex brush-like texture that differentially supports adjacent structures to protect the cellular structure of the resorbable osteoconductive matrix from osteoinductive material loss from compression. Additionally, the brush like texture can provide a frictioned surface that resists slippage against adjacent surfaces and that securely fits to adjacent surfaces.

In a preferred method of making the nanofiber-containing matrix, nanofibers are dispersed in a collagen dispersion, which is then dried while agitated to a thin matrix or sheet. The collagen dispersion can be derived by any known process. For example, U.S. Pat. No. 3,157,524, and U.S. Pat. No. 3,520,402 disclose collagen dispersion preparations. These references disclose forming tendon collagen slices in an acid solution to form a dispersion that is then extruded into a coagulating bath. In particular, the collagen dispersion can be prepared according to the disclosure of Narotam U.S. Pat. No. 5,997,895, assigned to Integra Lifesciences Corporation. The disclosure of U.S. Pat. No. 5,997,895 is incorporated herein by reference in its entirety.

In the procedure set forth in U.S. Pat. No. 5,997,895, a native source of Type I collagen, such as skin, tendon, ligament or bone, is first mechanically or hand cleaned of fat, fascia and other extraneous matter and washed. The cleaned and washed collagen containing material is then comminuted, generally by slicing or grinding. The material is then subjected to an enzyme treatment while under intermittent stirring with a proteolytic enzyme, such as ficin or pepsin so as to remove non-collagenous impurities that could cause antigenic activity. The enzyme treatment also swells the collagen by removing elastin. The amount of enzyme added to the collagen material and the conditions under which enzyme digestion takes place is dependent upon the particular enzyme used. Generally, when using ficin, which is commonly used, the pH is adjusted to about 6.0 to 6.3, and the collagen material is digested for about 1 to 2 hours at a temperature of about 36.5° C. to 37.5° C. with one part ficin for 150 parts of collagen material. After a requisite amount of time, the enzyme is inactivated, for example by adding a solution of an oxidizing agent, such as sodium chlorite (when the enzyme is ficin).

The enzyme treated collagen containing material is washed to remove excess enzyme and non-collagenous protein impurities. Preferably, the washing is carried out with ultrafiltered and deionized water. The collagen may be further washed with dilute aqueous hydrogen peroxide.

The enzyme digested collagen containing material can then be subjected to an alkali treatment at a pH of about 13 to 14, at a temperature of about 25° C. to 30° C. for a period of about 35 to 48 hours, preferably about 40 hours. The alkali treatment can be carried out in an aqueous solution of 5% sodium hydroxide and 20% sodium sulfate. Alkali treatment removes contaminating glycoproteins and lipids. The solution is then neutralized with a suitable acid, such as aqueous sulfuric acid, and thoroughly washed.

The collagen material is then further swollen with a suitable acid solution that does not cause cross-linking of the collagen. Suitable acids include acetic acid, hydrochloric acid and lactic acid. The acid is used to adjust the pH of the acid collagen dispersion to about 2 to 3.

The dispersed collagen mixture is then homogenized, for example in a blender or homogenizer, so as to further disassociate the fibers. The mixture is then filtered to remove unswollen, non-collagenous material; for example, by passing the dispersion through a 100 mesh stainless steel screen.

The nanofibers of the invention are added to the strained dispersion in a weight percent calculated on a number of nanofibers per unit volume of matrix, preferably per unit volume of collagen matrix. For example, a weight percent added nanofiber can be calculated to provide 1 nanofiber per 10 micron$^3$ to 200 nanofibers per micro$^3$ of collagen matrix volume. Then the collagen matrix with nanofiber dispersion is poured into a suitable tray. The dispersion is frozen and lyophilized while agitated for about 1 to about 48 hours.

Mechanical agitation of the solidifying dispersion assures a random orientation of nanofibers so that at least a portion of nanofiber ends protrude from a surface of a solidified collagen matrix surface. The agitation can be applied uniformly to provide uniformly bristled surfaces. Or, the agitation can be selectively applied to produce selected bristled surfaces. The agitation can be applied for example, by low-frequency sonication or by rocking the tray or stirring the solidifying dispersion. In one example, agitation is applied by ultrasonic vibration at a frequency between 2 kHz to less than 20 kHz, or at a frequency between 3 kHz to 10 kHz, preferably at a frequency between 4 kHz to 8 kHz. The agitation is applied until the dispersion has sufficiently solidified to support at least some of the nanofibers in an orientation that projects ends through matrix surface to form the invention bristled surface. The protrusion of bristled ends above the collagen matrix surface can be non-uniform between 1 nm to 1000 nm or between 10 nm to 500 nm or 100 nm to 300 nm. Protrusion of any degree of the length of the bristles provides improved load bearing tensile strength compared to surface attached nanofibers. The protrusion can be defined as at least 0.1% average length to 99% average length beyond the matrix surface, desirably from 1% to 90% and preferably 10% to less than 50% average length protrusion of nanofibers beyond the matrix surface.

The resulting bristled sponge can have a thickness from 2.0 mm to 6 mm, preferably about 3 mm. The density of the nanofiber-containing dispersion and the lyophilization cycle dictate the sponge density and pore size. The bristled collagen matrix has pores of a sufficient size and quantity to permit infiltration of growing tissue. The pore size can range from 10 μm to 500 μm, preferably from 50 μm to 150 μm, with surface pores being smaller than cross-sectional (internal) pores.

A film according to the invention can be provided by casting a dispersion of the nanofiber containing collagen having a collagen concentration of 0.1 to 10% solids (w:v) and 0.005 to 0.5% (w:w on collagen solids) of a suitable biocompatible plasticizer, such as glycerin. The plasticizer concentration can be about 0.1% and the collagen concentration about 1%, preferably 0.75% and the nanofiber concentration can be from 0.01% to 50%, desirably 0.1% to 10% and preferably 1% to 5%. A volume of the dispersion is poured into a suitable non-stick container and evaporated to provide a film having a thickness of 0.05 to 2.0 mm, preferably about 0.5 mm. The film can be cross-linked with heat or a suitable chemical cross-linking agent.

In another method, a collagen sponge or film is cast from lactic acid derived collagen fibers containing the nanofibers. The collagen fibers are produced by a process comprising dispersing a virus and prion free collagen source such as alkali-treated bovine tendon slices, in an aqueous solution of lactic acid, homogenizing the dispersion, filtering the homogenized lactic acid dispersion, and precipitating collagen fibers from the homogenized lactic acid dispersion by addition of aqueous ammonium hydroxide sufficient to adjust the pH to about 4.6-4.9.

A collagen sponge and film laminate can be prepared by casting a collagen film; drying the film; casting a nanofiber-containing collagen slurry onto the dried film; lyophilizing the slurry/film combination; and cross-linking the lyophilized laminate product by exposing it to vapors from an aqueous formaldehyde solution (preferably having a 9.6% formaldehyde concentration) for about ninety minutes at about 25° C., followed by forced air ventilation for about one hour.

Once implanted, the collagen sponge undergoes resorbtion over a 4 to 12 week period via cell-mediated degradation by macrophages. The collagen can provide a favorable surface for cell attachment during early osteoid formation. It then undergoes resorbtion. A collagen matrix, such as an absorbable collagen sponge, possesses all the properties of an ideal carrier for many biological agents and is particularly suited to carry all types of bone morphogenetic materials, including rhBMP-2. In one embodiment, the bone morphogenetic material can be BMP-1, BMP-2, BMP-3, BMP-4, BMP-5, BMP-6, BMP-6, BMP-7, BMP-8, BMP-9, BMP-10, and BMP-11.

Other embodiments of the present invention include use of the vacuum package container disclosed herein in conjunction with an INFUSE® Bone Graft device (Medtronic Sofamor Danek, Memphis, Tenn.) and can include a Bone Graft/LT-CAGE® Lumbar Tapered Fusion Device (Medtronic Sofamor Danek, Memphis, Tenn.) disposed within the Vacuum Infused Packake (VIP) medical container. The INFUSE® device comprises two parts: (1) a genetically-engineered human protein (rhBMP-2) to stimulate bone healing, and; (2) an absorbable collagen sponge scaffold made from cow (bovine) collagen that carries the BMP, as described above.

In yet further embodiments, the vacuum packaging can also contain other items disposed within it such as mechanical devices including metal plates, pins, rods, wires, screws, and Graft/LT-CAGE's® or any other suitable structural element either singularly or in combination with a porous substrate.

Freeze-dried (lyophilized) porous substrate, such as an absorbent matrix, can be difficult to hydrate and is often ineffectually hydrated in the operating room (OR) due to the amount of time it takes to hydrate the porous substrate using conventional "soaking" methods. The medical container disclosed herein embodies a novel method for rapidly rehydrating a porous substrate, decreasing the brittleness of the substrate, and delivering biological components and cells to the porous substrate in an effective and efficient manner. The container seals a dehydrated porous substrate under an extremely strong vacuum by evacuating the air from the pores of the substrate. During fluid infusion, the vacuum pulls the fluid into the porous substrate, rapidly infusing the pores and rehydrating the implant.

EXPERIMENTS

The following examples teach medical implants and methods and systems for hydrating and seeding medical implants with biological components. These examples are illustrative only and are not intended to limit the scope of the invention disclosed herein. The treatment methods described below can be optimized using empirical techniques well known to those of ordinary skill in the art. Moreover, artisans of skill would be able to use the teachings described in the following examples to practice the full scope of the invention disclosed herein.

Experiment 1

An experiment was conducted using an aqueous solution containing a known concentration of rhBMP-2 and multiple ACS sponges. 150 µg of rhBMP-2 (Infuse®, Medtronic, Inc., Memphis, Tenn.) per cc of carrier was delivered into absorbable collagen sponges (ACS, Medtronic, Inc.), using either a drip (soaking) method or via Vacuum Infused Packaging (VIP). The rhBMP-2 applied by the drip method was allowed to soak for 15 minutes while the VIP samples were only allowed 1 minute for binding. Unbound rhBMP-2 was rinsed out of the ACS sponges by being placed in excess saline on an orbital shaker at 37° C. for 1 hour. An rhBMP-2 ELISA kit (Leinco Technologies, Inc., St. Louis, Mo.) was used to determine the amount of rhBMP-2 that was bound to the ACS samples after the 1 hour rinse. Data were then analyzed using a one-way ANOVA ($p<0.05$) and Tukey's post-hoc honest significant difference test for multiple comparisons.

Figure 6:
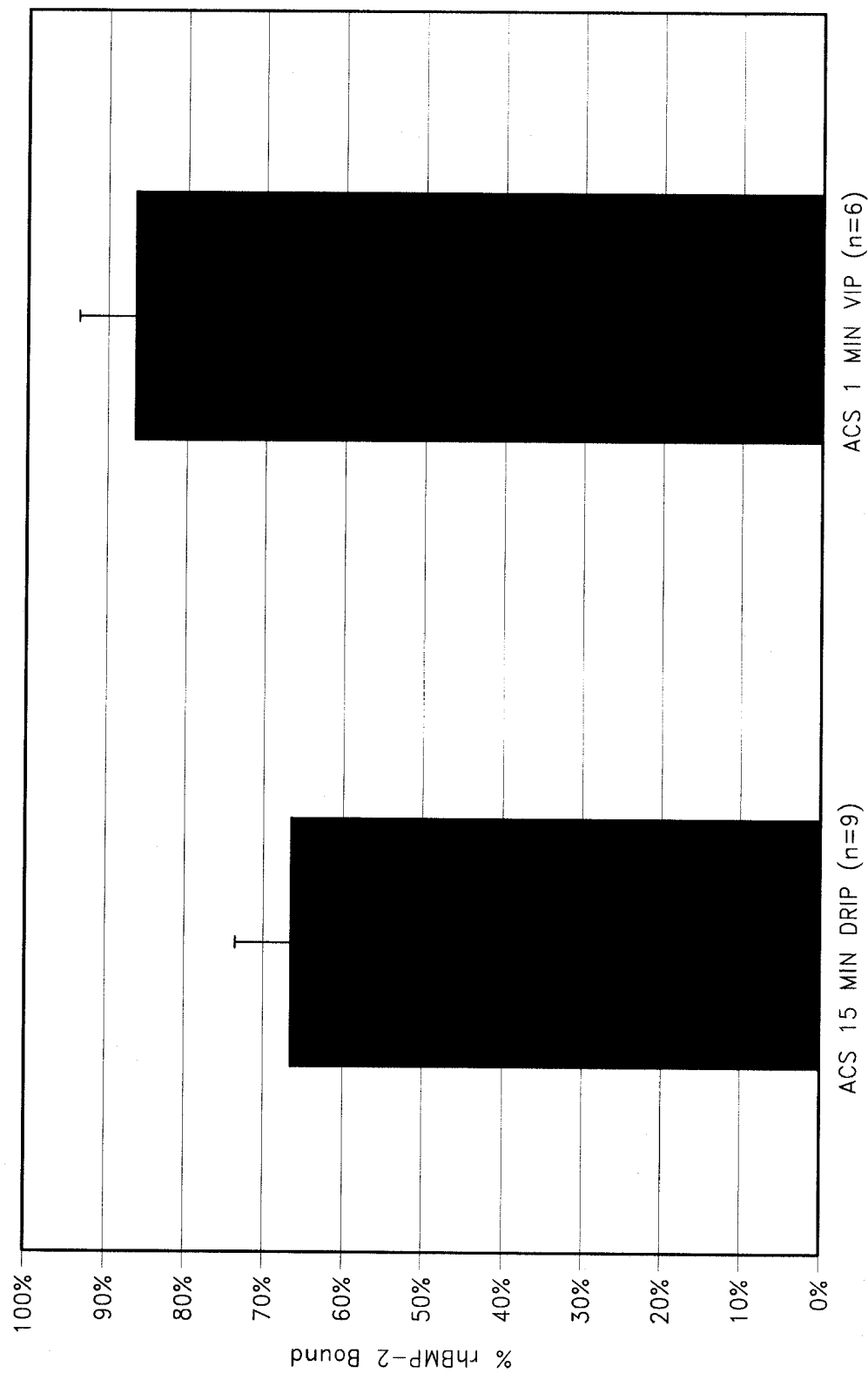

The amount of rhBMP-2 bound to the dripped ACS after 15 minutes of binding time versus ACS after 1 minute VIP infusion time is shown in FIG. 6. Some ACS sponges were soaked in rhBMP-2 solution (DRIP) and other ACS sponges were infused (using the same rhBMP-2 solution) inside of a vacuum sealed package. As can be seen in FIG. 6, the VIP infused ACS exhibited statistically greater binding of rhBMP-2 as compared to the 15 minute soaked (DRIP) ACS, even with a substantially lessened binding time of only 1 minute compared to the 15 minutes allotted to the soaked ACS ($p<0.0035$). These surprising and unexpected results indicate that VIP increases the binding ability of rhBMP-2 to ACS material. Without being bound to a particular theory, it is believed that the rhBMP-2 binds better to the ACS using VIP over traditional soaking methods because VIP facilitates greater binding by exposing the rhBMP-2 to a greater number of collagen binding sites within the ACS.

Experiment 2

A similar experiment was performed using allograft bone tissue, instead of ACS sponges, to further verify that the foregoing "surprising and unexpected" results were not unique to ACS sponges. 150 µg of rhBMP-2 (Infuse®, Medtronic, Inc., Memphis, Tenn.) per cc of carrier was delivered to multiple allograft bone tissue samples using either a drip (soaking) method or via Vacuum Infused Packaging (VIP). The rhBMP-2 applied by the drip method was allowed to soak for 15 minutes while the VIP samples were only allowed 1 minute for binding. Unbound rhBMP-2 was rinsed out of the allograft bone tissue samples by placing them in excess saline on an orbital shaker at 37° C. for 1 hour. An rhBMP-2 ELISA kit (Leinco Technologies, Inc., St. Louis, Mo.) was used to determine the amount of rhBMP-2 that was bound to the allograft bone tissue samples after the 1 hour rinse. Data were then analyzed using a one-way ANOVA ($p<0.05$) and Tukey's post-hoc honest significant difference test for multiple comparisons.

Figure 7:
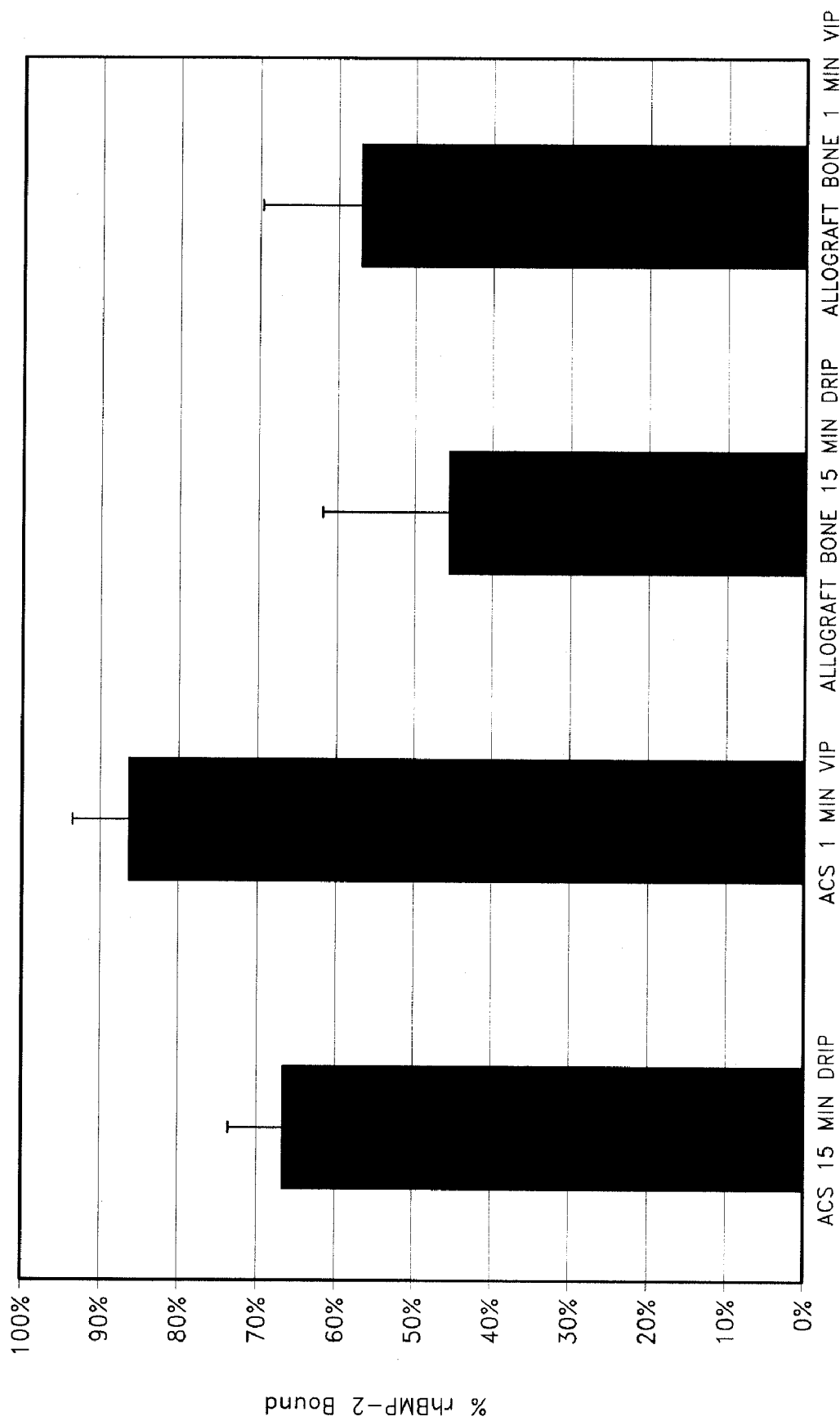

FIG. 7 shows the relative amounts of rhBMP-2 bound to the dripped allograft bone tissue samples after 15 minutes of binding time versus bone samples having a 1 minute VIP infusion time. As is seen in FIG. 7, the VIP infused allograft bone samples exhibited statistically greater binding of rhBMP-2 as compared to the 15 minute soaked (DRIP) allograft bone samples, even with a substantially lessened binding time of only 1 minute compared to the 15 minutes allotted to the soaked bone samples. These surprising and unexpected results further indicate that VIP increases the binding ability of rhBMP-2 in multiple absorbent matrix materials, not just in ACS sponges.

In one embodiment, the medical implant vacuum infused package container system provides greater than 50% binding of biological components to a bioabsorbable absorbent matrix in less than 15 minutes from infusion. In other embodiments, the medical implant vacuum infused package container system provides greater than 50% binding of biological components to a bioabsorbable absorbent matrix in less than 14, 13, 12, 11, 10, 9, 8, 7, 6, 5, 4, 3 or 2 minutes from infusion, and preferably in less than or equal to 1 minute from infusion.

In other embodiments, the medical implant vacuum infused package container system provides greater than 75% binding of biological components to a bioabsorbable absorbent matrix in less than 15 minutes from infusion. In other embodiments, the medical implant vacuum infused package container system provides greater than 75% binding of biological components to a bioabsorbable absorbent matrix in less than 14, 13, 12, 11, 10, 9, 8, 7, 6, 5, 4, 3 or 2 minutes from infusion, and preferably in less than or equal to 1 minute from infusion.

The benefits of increased binding between rhBMP-2 and ACS in a VIP environment are immediate and identifiable. Strong binding of rhBMP-2 to ACS is very desirable because this lessens premature precipitation of rhBMP-2 out of absorbent matrix grafts and into surrounding tissue inside the patient's body. As discussed previously, premature or excessive precipitation of BMPs has been known to stimulate ectopic bone growth in muscle tissue and in more serious cases, involving implants in the cervical spinal area, ectopic bone growth has been known to completely surround the subject's trachea closing off their air passage and causing suffocation.

It is to be understood that the detailed description and specific examples, while indicating preferred embodiments of the present invention, are given by way of illustration and not limitation. Many changes and modifications within the scope of the present invention can be made without departing from the spirit thereof, and the invention includes all such modifications.

What is claimed is:

1. A system for loading bone morphogenetic material into a medical graft, comprising:
    a hermetically sealed container comprising an entry port, a substrate cavity, and top, side and bottom walls defining an inner surface of the container, a lip surrounding a periphery of the substrate cavity and the top wall is hermetically sealed to the lip adjacent the substrate cavity periphery;
    the entry port configured to receive the bone morphogenetic material;
    the substrate cavity in communication with the entry port and having the medical graft stored and maintained under negative pressure; and
    wherein a container volume is substantially the same as a volume of the medical graft.

2. The system of claim 1, wherein the entry port is disposed near the middle of the medical graft within the substrate cavity.

3. The system of claim 1, wherein the container further comprises one or more supporting members configured to elevate and support the container in a substantially stable position.

4. The system of claim 1, wherein said bone morphogenetic material is selected from the group consisting of bone morphogenetic protein (BMP), transforming growth factor β (TGF-β) growth differentiation factor (GDF), and cartilage derived morphogenetic protein (CDMP).

5. The system of claim 4, wherein said bone morphogenetic protein is selected from the group consisting of BMP-1, BMP-2, BMP-3, BMP-4, BMP-5, BMP-6, BMP-7, BMP-8, BMP-9, BMP-10, and BMP-11.

6. The system of claim 4, wherein said bone morphogenetic material is a recombinant human bone morphogenetic protein.

7. The system of claim 6, wherein said recombinant human bone morphogenetic protein is rhBMP-2.

8. The system of claim 1, wherein said medical graft is a bioabsorbable absorbent matrix.

9. The system of claim 8, wherein said absorbent matrix comprises a purified collagen matrix.

10. The system of claim 9, wherein said collagen is selected from the group consisting of Type I collagen, Type II collagen, Type IV collagen, cell-contracted collagen, and combinations thereof.

11. The system of claim 9, wherein said collagen matrix comprises a nanofiber density of 10 nanofiber per 100 micron$^3$ collagen matrix volume.

12. A system for loading bone morphogenetic material into a medical graft, comprising:
    a hermetically sealed container comprising an entry port configured to receive the bone morphogenetic material, and top, side and bottom walls defining a substrate cavity, a lip surrounding a periphery of the substrate cavity and the top wall is hermetically sealed to the lip adjacent the substrate cavity periphery;
    the entry port being disposed near the middle of the medical graft within the substrate cavity,
    the substrate cavity in communication with the entry port and having the medical graft stored and maintained under negative pressure; and
    wherein a container volume is substantially the same as a volume of the medical graft.

13. The system of claim 12, wherein the container further comprises one or more supporting members configured to elevate and support the container in a substantially stable position.

14. The system of claim 12, wherein said bone morphogenetic material is selected from the group consisting of bone morphogenetic protein (BMP), transforming growth factor β (TGF-β), growth differentiation factor (GDF), and cartilage derived morphogenetic protein (CDMP).

15. The system of claim 14, wherein said bone morphogenetic protein is selected from the group consisting of BMP-1, BMP-2, BMP-3, BMP-4, BMP-5, BMP-6, BMP-7, BMP-8, BMP-9, BMP-10, and BMP-11.

16. The system of claim 14, wherein said bone morphogenetic material is a recombinant human bone morphogenetic protein.

17. The system of claim 16, wherein said recombinant human bone morphogenetic protein is rhBMP-2.

18. The system of claim 12, wherein said medical graft is a bioabsorbable absorbent matrix.

19. The system of claim 18, wherein said absorbent matrix comprises a purified collagen matrix.

20. The system of claim 19, wherein said collagen is selected from the group consisting of Type I collagen, Type II collagen, Type IV collagen, cell-contracted collagen, and combinations thereof.

21. The system of claim 19, wherein said collagen matrix comprises a nanofiber density of 10 nanofiber per 100 micron$^3$ collagen matrix volume.

* * * * *